United States Patent [19]

Hazard

[11] Patent Number: 4,859,184
[45] Date of Patent: * Aug. 22, 1989

[54] FACE SHIELD DEVICE

[76] Inventor: James T. Hazard, 311 Fairmeade Rd., Louisville, Ky. 40207

[*] Notice: The portion of the term of this patent subsequent to Oct. 20, 2004 has been disclaimed.

[21] Appl. No.: 98,808

[22] Filed: Sep. 21, 1987

Related U.S. Application Data

[63] Continuation-in-part of Ser. No. 842,824, Mar. 3, 1986, Pat. No. 4,701,129.

[51] Int. Cl.⁴ .............................................. A61C 5/14
[52] U.S. Cl. ................................ 433/136; 433/229; 250/515.1
[58] Field of Search ................ 433/136, 137; 2/2.5, 2/49 R, 49 A, 11; 128/132 R; 248/444; 250/515.1

[56] References Cited

U.S. PATENT DOCUMENTS

| | | | |
|---|---|---|---|
| 607,496 | 7/1898 | Watson | 248/444 |
| 628,923 | 7/1899 | Carmichael | 433/137 |
| 1,313,908 | 8/1919 | Polasky | 2/11 |
| 1,906,539 | 5/1933 | Church | 2/11 |
| 2,564,952 | 8/1951 | Blasius | 2/11 |
| 2,589,320 | 3/1952 | Allenbrook | 248/444 |
| 3,707,004 | 12/1972 | Kapitan et al. | 2/2.5 |
| 4,286,170 | 8/1981 | Motl | 250/515.1 |
| 4,701,129 | 10/1987 | Hazard | 433/229 |

FOREIGN PATENT DOCUMENTS

| | | | |
|---|---|---|---|
| 2442881 | 3/1976 | Fed. Rep. of Germany | 2/2.5 |
| 0095151 | 3/1939 | Sweden | 2/11 |

*Primary Examiner*—John J. Wilson
*Assistant Examiner*—Adriene J. Lepiane
*Attorney, Agent, or Firm*—Charles G. Lamb

[57] ABSTRACT

A face shield device for protecting the wearer's eyes and face from debris, bacteria, and the like includes an arcuate transparent face shielding panel and a support for holding the face shielding panel in front of and spaced outwardly away from the wearer's face. The support is attached to the face shielding panel and lays on the wearer's chest. In one embodiment, the support is suspended from the wearer's neck by a flexible band which fits around the wearer's neck. In another embodiment, the support is suspended from the wearer's shoulders by shoulder engaging hook members. The face shield device may also include means to protect the wearer from ultra-violet radiation or other types of radiation harmful to the face and eyes.

5 Claims, 2 Drawing Sheets

FACE SHIELD DEVICE

Cross-Reference to Related Application

This is a continuation-in-part of application Ser. No. 842,824, filed Mar. 3, 1986 now U.S. Pat. No. 4,701,129, issued Oct. 20, 1987.

BACKGROUND OF THE INVENTION

The present invention relates to face and eye protectors or shields, and more particularly to a face and eye shield which is supported at the wearer's chest and extends in front of and spaced outwardly from the wearer's face.

In the last few years there has developed a lot of interest in the dental profession of the transfer of bacteria from patient to dentist. This is caused predominantly because dentists are subjected to debris from a patients mouth while working on the patient. This debris comprises particles of tooth, filling material, water, and air borne particles coming from the oral cavity.

Moreover, there are new processes for repairing teeth which require the use of ultra violet radiation. In the use of equipment which emits this radiation, the eyes of the dentist or their assistant is subjected to this radiation which is harmful to the eyes.

SUMMARY OF THE INVENTION

It is an object of the present invention to protect the wearer's face and eyes from debris.

It is another objective of the present invention to provide a face and eye shield of the class described which will not hinder the wearer's vision and freedom of movement.

It is a further objective of the present invention to provide a face and eye shield of the class described which is comfortable to wear.

Other objectives will become apparent to those skilled in the art upon reading the disclosure set forth hereinafter.

More particularly, the present invention provides a face and eye shield device comprising a transparent face and eye shielding panel, and means supporting the face shielding panel at the wearer's chest and holding the face shielding panel in front of and spaced outwardly from the wearer's face.

BRIEF DESCRIPTION OF THE DRAWINGS

The present invention will become even more clear upon reference to the following description in conjunction with the accompanying drawings in which like numbers refer to like parts throughout the several views and wherein.

DETAILED DESCRIPTION OF THE PREFERRED EMBODIMENT

Figure 1:
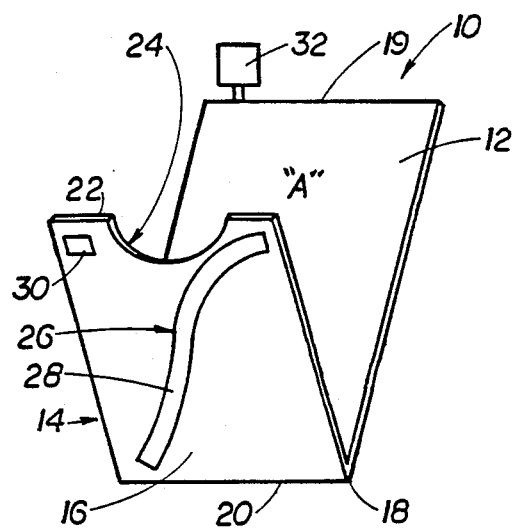
FIG. 1 is a perspective view of one embodiment of the present invention.
Figure 5:
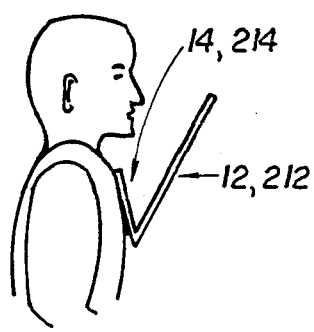
FIG. 5 is a side view depicting a person wearing any of the embodiments of FIGS. 1-4.

With reference to FIG. 1, there is shown a face and eye shield device 10 of the present invention. As shown, the face and eye shield device, generally denoted as the number 10, includes a transparent face shielding panel 12 and support means, generally denoted as the number 14, for supporting the face shielding panel 12 at the wearer's chest and holding the face shielding panel 12 in front of and spaced outwardly from the wearer's face as shown in FIG. 5.

The supporting means 14 is illustrated as a support panel 16 adapted to lay on the wearer's chest, and the support panel 16 is structurally associated with the face shielding panel 12. More particularly, the shielding panel 12 and the face supporting panel 16 are joined together at their lower edges 18 and 20, respectively. Preferably, the face shielding panel 12 and supporting panel 16 are formed of a single sheet of transparent material which is folded at the bottom edge 18 of the shielding panel 12 and bottom edge 20 of the supporting panel 16. The supporting panel 16 and face shielding panel 12 cooperate to define an acute included angle "A" therebetween with the apex of the angle being the lower edges 18 and 20 of the face shielding panel 12 and supporting panel 16.

Generally, the face shield panel 12 has a larger height dimension measured from the lower edge 18 to the top edge 19 than the height dimension of the supporting panel 16 measured from the lower edge 20 to the top edge 22. And, in one embodiment the top edge 22 of the supporting panel 16 is formed with a centrally located notched out area 24 configured and sized to receive therein the wearer's throat.

The face and eye shield device 10 further includes means, generally denoted as the numeral 26, for suspending the face shield device 10 from the wearer's neck. As shown, the suspending means 26 is a flexible neck band or belt 28 connected to the supporting panel 16 proximate the top edge 22 of the supporting panel 16 adopted to fit around the wearer's neck. Toward this objective the flexible neck band 28 is attached at one end to the chest contact surface of the supporting panel 16 next to one side of the throat receiving notch 24. A neck band fastener 30 is attached to the chest contact surface of the supporting panel 16 next to the other side of the throat receiving notch 24. The free end of the neck band 28 can be adjustably connected to the fastener 30 when the neck band 28 has been located across the wearer's neck. Virtually any conventional or otherwise convenient fastener can be used. One contemplated type fastener is formed of "VELCRO TM".

As an optional feature, for example, an X-ray slide holder 32 may be attached to the top edge 19 of the face shielding panel 12 to one end of the shielding panel top edge 19 so that it will not obstruct the wearer's straight ahead vision, but will be conveniently positioned for viewing by the wearer merely glancing upwardly and to one side. Other features may include measuring devices incorporated on the shield, and means to prevent other types of radiation from penetrating through the shield, such as those emitted from laser beams and the like.

Figure 2:
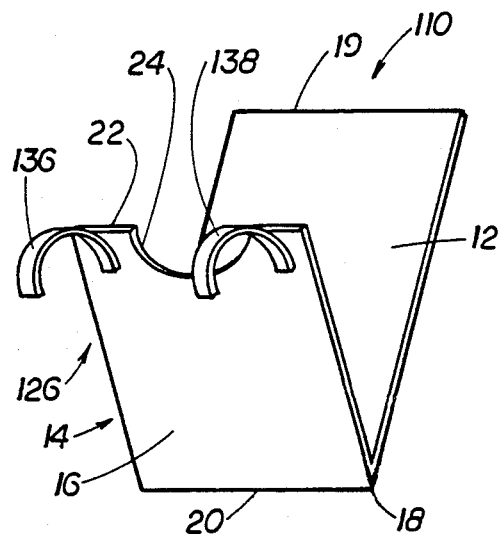
FIG. 2 is a perspective view of another embodiment of the present invention.

With reference to FIG. 2, there is shown a somewhat different embodiment of a face and eye shield device, generally denoted as the numeral 110, of the present invention. The face and eye shield device 110 is identical to the face and eye shield 10 of FIG. 1 in every respect except for the suspending means, generally denoted as the numeral 126. Therefore, all features in common with the face and eye shield 10 are denoted by the same numerals, and for the sake of brevity, the description of these common features will not be repeated.

The suspending means 126 of the face and eye shield device 110 suspends the face and eye shield device 110 from the wearer's shoulders. Toward this objective, the suspending means 126 comprises a pair of spaced apart shoulder engaging hook members 136 and 138 attached to the supporting panel 16 proximate the top edge 22 to either side of the throat receiving notched out area 24. The engaging hook members 136 and 138 open downwardly and are sized, configured and spaced apart by an appropriate distance to comfortably receive the wearer's shoulders.

Figure 3:
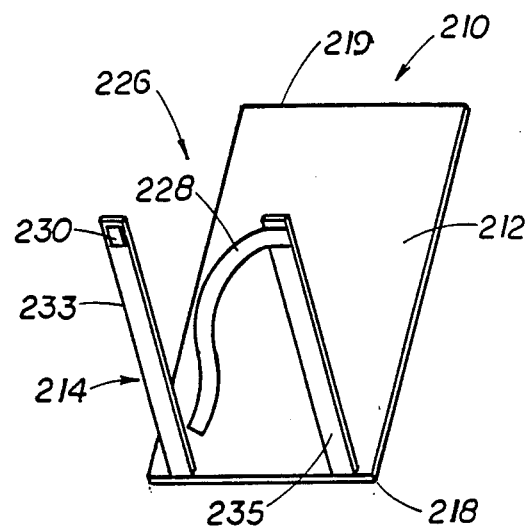
FIG. 3 is a perspective view of a further embodiment of the present invention.

Referring now to FIG. 3, there is shown another embodiment of a face and eye shield device, generally denoted as the numeral 210, of the present invention.

As shown, the face and eye shield device 210 includes a transparent face shielding panel 212 and supporting means, generally denoted as the numeral 214, for supporting the face shielding panel 212 at the wearer's chest and holding the face shielding panel 212 in front of and spaced outwardly from the wearer's face as shown in FIG. 5.

The supporting means 214 is shown as a pair of spaced apart rigid straps 233 and 235 joined at their lower ends to the face shield panel 21 proximate the lower edge 218 of the face shield panel 212 and extending upwardly therefrom. The straps 233 and 235 are adapted to lay on the wearer's chest and should be spaced apart by an appropriate distance wider than the wearer's neck. The rigid supporting straps 233 and 235 each cooperate with the face shielding panel 212 to define an equal acute included angle "A" between the support strap 233 and 235 and face shielding panel 212.

The face shield panel 212 has a larger height dimension measured from the lower edge 218 to the top edge 219 than the length of the straps 233 and 235 as measured from lower strap ends attached to the face shield panel and the top distal ends of the straps 233 and 235.

The face and eye shield device 210 further includes means, generally denoted as the numeral 226, for suspending the face shield device 210 from the wearer's neck. As shown, the suspending means 226 is a flexible band 228 connected to the top distal ends of the rigid supporting straps 233 and 235 adapted to fit around the wearer's neck. Toward this objective, the flexible neck band 228 is attached at one end to one of the supporting straps 235. A neck band fastener is attached to the top distal end of the supporting strap 233 The free end of the neck band 228 can be adjustably connected to the fastener 230 when the neck band 228 has been located across the wearer's neck.

Figure 4:
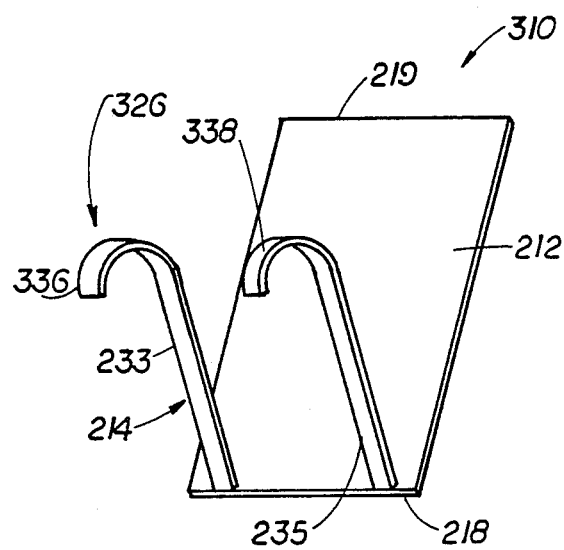
FIG. 4 is a perspective view of yet another embodiment of the present invention.

With reference to FIG. 4, there is illustrated a somewhat different embodiment of a face and eye shield device, generally denoted as the numeral 310, of the present invention. The face and eye shield 310 is identical to the face and eye shield 210 of FIG. 3 in every respect except for the suspending means, generally denoted as the numeral 326. Therefore, all of the features in common with the eye shield 210 are denoted by the same numerals, and for the sake of brevity, the description of these common features will not be repeated.

The suspending means 326 of the face and eye shield device 310 suspends the face and eye shield 310 from the wearer's shoulders. Toward this objective, the suspending means 326 comprises a pair of spaced apart shoulder engaging hook members 336 and 338 at the top or distal ends of the support straps 233 and 235. Preferably, the hook members 336 and 338 are integrally formed in the top of distal end of each of the support straps 233 and 235. The shoulder engaging hook members 336 and 338 open downwardly and are sized, configured and spaced apart from each other by an appropriate distance to comfortably receive the wearer's shoulders on either side of the wearer's neck.

As an additional feature of the invention, the face shielding panel in each of the above-described embodiments may include an ultra-violet blocking material in the area of FIG. 1 denoted by the letter "A".

Figure 6:
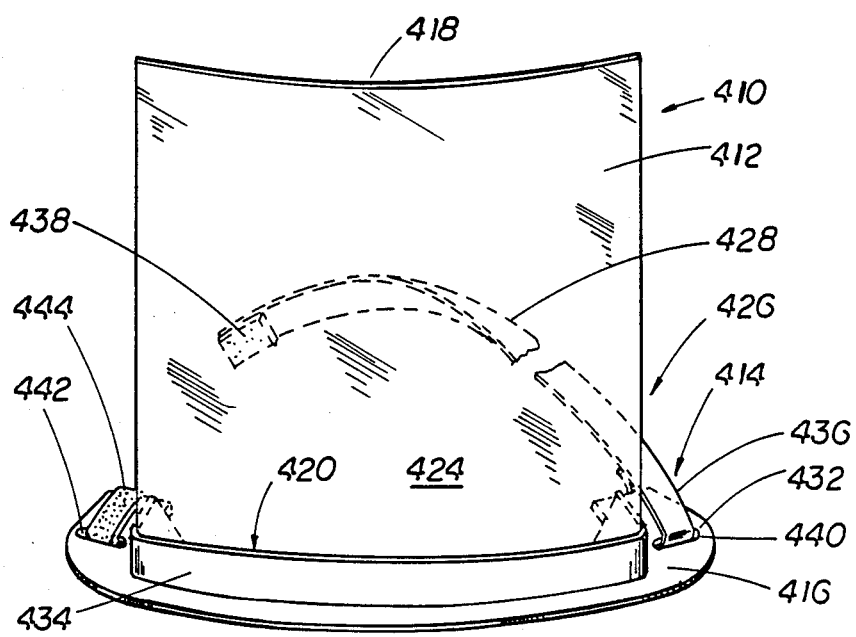
FIG. 6 is a perspective schematic front view of even another embodiment of the present invention; and, FIG. 7 is a side view of the present invention shown in FIG. 6 depicting a person wearing it.
Figure 7:
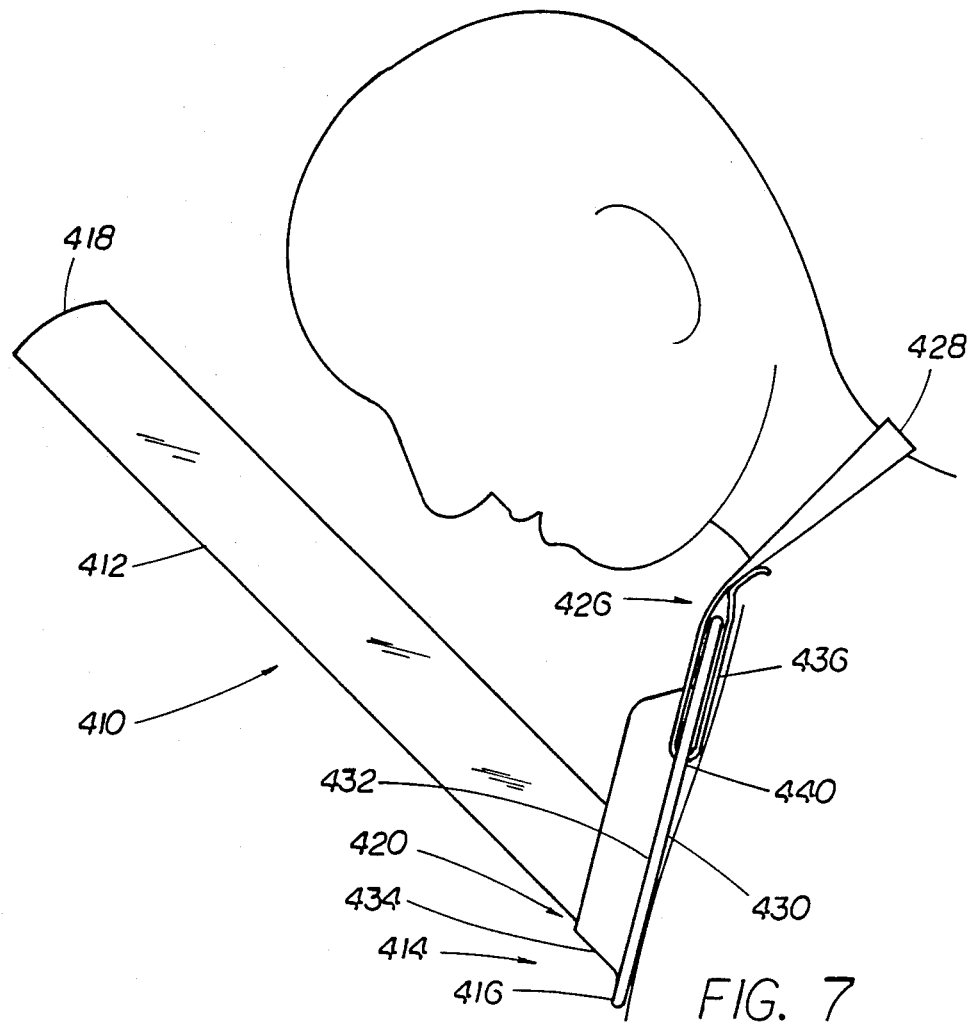

With reference to FIGS. 6 and 7, there is shown another face and eye shield device 410 of the present invention. As shown, the face and eye shield device includes an arcuate transparent face shielding panel 412 and support means, generally denoted as the numeral 414, for supporting the face shielding panel 412 at the wearer's chest and holding the face shielding panel 412 in front of and spaced outwardly from the wearer's face as shown in FIG. 7. The face shielding panel 412 extends outwardly from the wearer's chest at an acute angle to the vertical. The height of the face shield panel 412 is such that the wearer's head is tilted forwardly toward the wearer's chest, the face shielding panel 412 extends across the breadth and height of the wearer's face, and when the wearer's head is in an upright position, the top edge 418 of the face shielding panel 412 is generally below the wearer's line of sight. The shielding panel 412 does not extend to or around the sides of the wearer's head.

The supporting means 414 is illustrated as a support panel 416 adapted to lay on the wearer's chest, and the support panel 416 is structurally associated with the face shielding panel 412. More particularly, the bottom edge 420 of the shielding panel 412 is joined to the face shield support panel 416. The support panel 416 is arcuately formed to define a centrally located area 424 configured and sized to provide a clearance for the wearer's face and throat. The support panel 416 has a generally flat bottom side 430 for resting against the wearer's chest, and a top side 432. An arcuate flange 434 extends upwardly from the top side 432 of the support panel 416 positioned in abutting contact with the convex side of the arcuate face shielding panel 416 proximate the bottom edge 420 of the face shielding panel 416. The face shield panel 416 is affixed to the flange 434 by any convenient means such as mechanical fasteners, or as shown by an adhesive.

The face and eye shield device 410 further includes means, generally denoted as the numeral 426, for suspending the face shield device 410 from the wearer's neck. As shown, the suspending means 426 is a flexible neck band or belt 428 connected at one of its ends to the supporting panel 416 proximate the end 436 of the supporting panel 416 adapted to fit around the wearer's neck and be removably attached at its free end 438 to the other end of the support panel. Toward this objective, the end 436 of the support panel 426 is formed with a slot 440 through which the fixed end of the neck band 428 is looped, and the other end 438 of the support panel 426 is formed with a slot 442 for receiving a fastener 444 for attaching the free end 438 of the neck band 428 to the support panel 416. Preferably, the fastener 444 is a section of one half of a hook and eye fastener, such as the fastener sold under the trademark "VELCRO TM" looped through the slot 442. The free end 438 of the neck band 428 includes the mating portion of the hook an eye fastener so that the free end of the neck band 428 can be adjustably positioned and attached to the end of the support panel 416.

The foregoing detailed description is given primarily for clearness of understanding and no unnecessary limitations are to be understood therefrom for modifications will become obvious to those skilled in the art upon reading this disclosure and may be made without departing from the spirit of the invention and scope of the appended claims.

What is claimed is:

1. A face shield device comprising:

An arcuate substantially completely transparent face shielding panel concavely oriented toward the wearer's face, the face shielding bracket having an arcuate bottom edge, an arcuate top edge, and generally parallel lateral side edges;

a shield support bracket having a bottom side for resting against the wearer's chest, and connected at a top side to the bottom edge of the shielding panel for holding the shielding panel at and extending outwardly from the wearer's chest at an acute angle to the vertical such that only when the wearer's head is tilted forwardly does the face shielding panel extend across the wearer's face; and, a flexible band connected at each of its ends to the shield support bracket, at least one of said ends being detachably connected.

2. The face shield device of claim 1, wherein when the wearer's head is in an upright position, the top edge of the face shielding panel is below the wearer's line of sight.

3. The face shield device of claim 1, wherein the shield support bracket is arcuate and is concavely oriented toward the wearer's neck when being worn.

4. The face shield device of claim 1, wherein the shield support bracket includes means for connecting the face shielding panel to the top side of the shield support bracket.

5. A face shield device comprising:

an arcuate substantially completely transparent face shielding panel concavely oriented toward the wearer's face, the face shielding panel having an arcuate bottom edge, an arcuate top edge, and generally parallel lateral side edges;

a shield support bracket arcuately formed to define a centrally located area configured and sized to provide a clearance for the wearer's face and throat, the support bracket has a generally flat bottom side for resting against the wearer's chest and a top side, an arcuate flange extending upwardly from the top side of the support bracket, and the arcuate flange being in abutting contact with the bottom edge of the face shielding panel and affixed to the face shielding panel for holding the face shielding panel at and extending outwardly from the wearer's chest at an acute angle to the vertical such that only when the wearer's head is tilted forwardly does the face shielding panel extend across the wearer's face and when the wearer's head is in an upright position the top edge of the face shielding panel is below the wearer's line of sight; and, a flexible band connected at each of its ends to a different one of the ends of the arcuate shield support bracket.

* * * * *